(12) United States Patent
Bruder et al.

(10) Patent No.: US 8,306,295 B2
(45) Date of Patent: Nov. 6, 2012

(54) METHOD FOR GENERATING COMPUTED TOMOGRAPHY IMAGE DATA RECORDS OF A PATIENT IN THE HEART CT SCAN DURING A PERFUSION CONTROL BY APPLYING CONTRAST AGENT

(75) Inventors: Herbert Bruder, Hōchstadt (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 536 days.

(21) Appl. No.: 12/585,580

(22) Filed: Sep. 18, 2009

(65) Prior Publication Data

US 2010/0074503 A1 Mar. 25, 2010

(30) Foreign Application Priority Data

Sep. 19, 2008 (DE) .......................... 10 2008 048 045

(51) Int. Cl.
*G06K 9/00* (2006.01)
*A61B 6/00* (2006.01)
(52) U.S. Cl. ............................. 382/128; 382/131; 378/8
(58) Field of Classification Search .................. 382/128, 382/131; 378/8
See application file for complete search history.

(56) References Cited

U.S. PATENT DOCUMENTS

| | | | | |
|---|---|---|---|---|
| 8,194,955 B2 * | 6/2012 | Sapp et al. | ..................... | 382/128 |
| 2003/0016851 A1 * | 1/2003 | Kaufman et al. | ............. | 382/131 |
| 2005/0058331 A1 * | 3/2005 | Klotz | ............................. | 382/131 |
| 2006/0235293 A1 | 10/2006 | Raupach et al. | | |
| 2007/0040831 A1 * | 2/2007 | Flohr et al. | | |
| 2008/0260230 A1 * | 10/2008 | Gotardo et al. | ................ | 382/131 |
| 2008/0269611 A1 * | 10/2008 | Pedrizzetti et al. | ............ | 600/454 |
| 2009/0129536 A1 * | 5/2009 | Ichihara et al. | ..................... | 378/4 |
| 2009/0161820 A1 | 6/2009 | Raupach | | |
| 2009/0161935 A1 | 6/2009 | Bruder et al. | | |
| 2011/0263973 A1 * | 10/2011 | Bernhardt et al. | ............. | 600/431 |

FOREIGN PATENT DOCUMENTS

| | | |
|---|---|---|
| DE | 10010279 A1 | 9/2001 |
| DE | 102005012654 A1 | 10/2006 |
| DE | 102005038940 A1 | 3/2007 |

OTHER PUBLICATIONS

Perona et al. "Scale-space and edge detection using anisotropic diffusion", IEEE Transactions on Pattern Analalysis and Machine Intelligence, vol. 12, pp. 629-639, 1990; Others; 1990.
J. Weickert, "Anisotropic Diffusion in Image Processing", Teubner-Verlag, Stuttgart, Germany, 1998, pp. 95-105; Book.

* cited by examiner

*Primary Examiner* — Alexander H Taningco
(74) *Attorney, Agent, or Firm* — Harness, Dickey & Pierce, P.L.C.

(57) ABSTRACT

A method is disclosed for generating computed tomography image data records of a patient in a heart CT scan during a perfusion control by applying contrast agent. In at least one embodiment, a plurality of temporally consecutive CT data records are recorded as an exposure series with a CT system and if necessary are reconstructed. These CT data records are improved for better visualization of the perfusion by way of electronic filtering and post-processing, with all projection and/or image data determined during a CT scan being used, however with the aid of frequency filtering only the data of a projection or of a reconstructed image for generating a final representation being used which does not fall within a predetermined local frequency range of a heart movement.

22 Claims, 5 Drawing Sheets

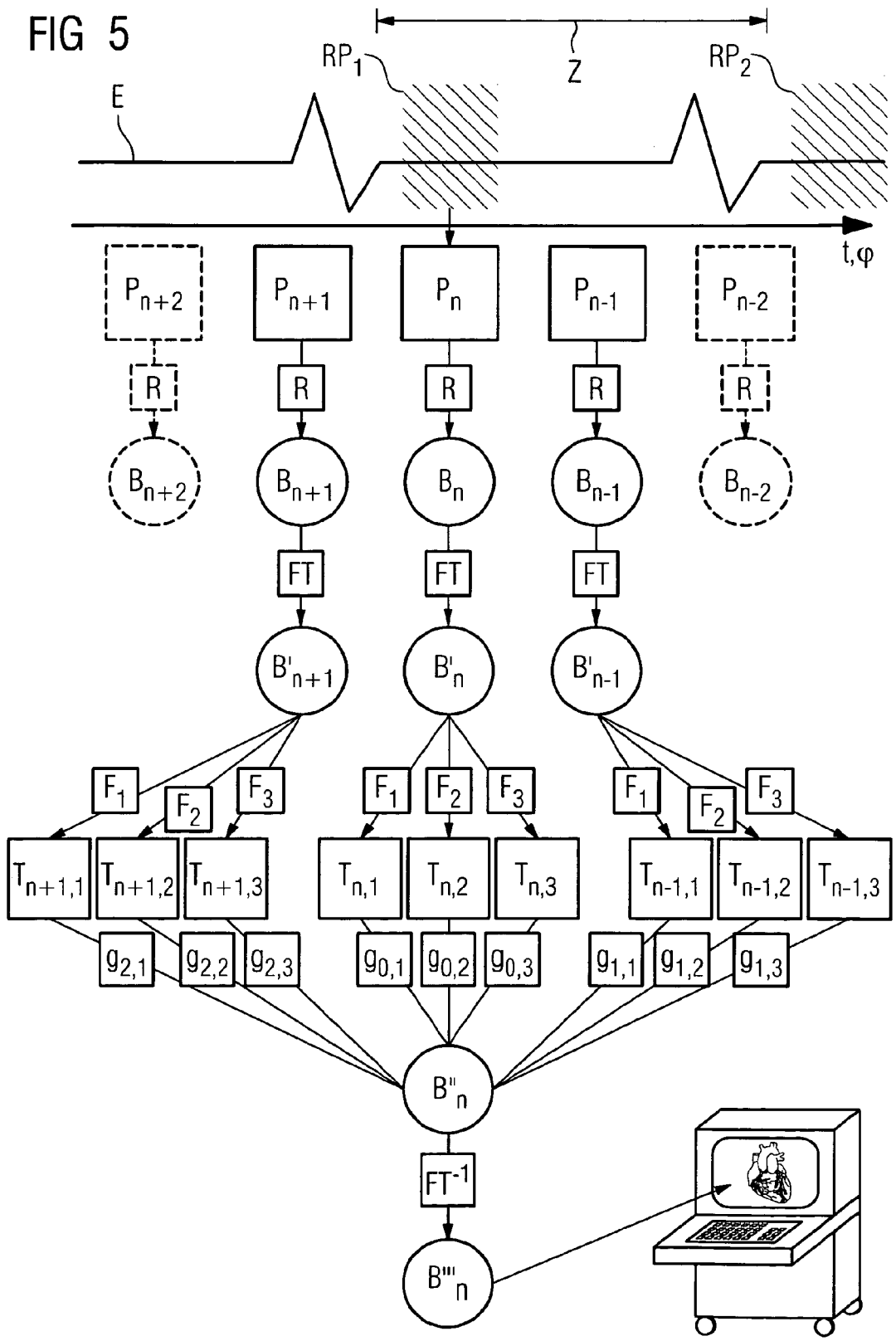

METHOD FOR GENERATING COMPUTED TOMOGRAPHY IMAGE DATA RECORDS OF A PATIENT IN THE HEART CT SCAN DURING A PERFUSION CONTROL BY APPLYING CONTRAST AGENT

PRIORITY STATEMENT

The present application hereby claims priority under 35 U.S.C. §119 on German patent application number DE 10 2008 048 045.2 filed Sep. 19, 2008, the entire contents of which are hereby incorporated herein by reference.

FIELD

At least one embodiment of the invention generally relates to a method for generating computed tomography image data records of a patient in the heart CT scan during a perfusion control by applying contrast agent, with a plurality of temporally consecutive CT data records being recorded with a CT system as an exposure series and if necessary being reconstructed and these CT data records being improved by electronic filtering and post-processing in order to improve the visualization of the perfusion.

BACKGROUND

Methods for increasing the quality of computed tomography exposure series by way of image processing are generally known. Reference is made for instance to the publication DE 10 2005 038 940 A1, in which an edge-maintaining filter is used to improve the image. The publications P. Perona and J. Malik, "Scale space and edge detection using anistropic diffusion", IEEE Transactions on Pattern Analysis and Machine Intelligence, Vol. 12, pages 629-639, 1990, and J. Weickert, "Anisotropic Diffusion in Image Processing", Teubner-Verlag, Stuttgart, Germany, 1998, disclose the use of diffusion filters in order to improve the image quality. Reference is also made to the publication DE 10 2005 012 654 A1, in which correlation calculations are used to filter image data in order also to improve the quality here. Each of the aforementioned publications are hereby incorporated herein by reference, in their entirety.

All these afore-cited known methods for improving the quality of image recordings by means of image processing nevertheless reach their limits if the relevant contrast is close to or even smaller than the noise. If CT perfusion examinations of the heart are examined, this indicates that the typical CT value changes, which are needed in order to identify the perfusion, lie in the range of approximately 2 to 20 HU, in other words 0.2 to 2% of the contrast between water and air. The image noise consequently plays a decisive role. To complicate matters further during the heart CT scan, the movement of the heart during the examination may result in motion blurs.

SUMMARY

At least one embodiment of the invention is directed to a method for improving the quality of computed tomography exposure series, which allows the signal-to-noise ratio to be reduced as much as possible on the one hand and as few motion blurs as possible to develop on the other hand.

The inventors have identified that these actually contradictory tasks can as a result be largely fulfilled in the case of a gated heart CT scan, if all projection and/or image data determined during a CT scan is used, with only the data of a projection or a reconstructed image being used with the aid of frequency filtering to generate a final representation which does not fall within a predetermined local frequency range of a heart movement. Conversely, data which falls within the typical local frequency range of a perfusion can even be weighted more significantly so that these changes in the observed tissue can be emphasized particularly clearly. In this way, additional image information also from heart phases, which cannot actually be evaluated, can nevertheless contribute to improving the image quality and thus also to improving the number of doses used in a CT examination.

According to this knowledge, the inventors propose, in at least one embodiment, the following method for generating computed tomography image data records of a patient in the heart CT scan during a perfusion control by applying contrast agent comprising:

scanning the patient within the region of the beating heart using an X-ray CT system and generating CT data records with correlated movement information relating to the heart during several heart cycles comprising several cycle phases, transforming the CT data records into a local frequency space, dividing at least one transformed CT data record into at least two transformed CT partial data records in each instance in accordance with different local frequency ranges, compiling a new transformed CT data record from several CT partial data records in each instance, with CT partial data records of at least one first local frequency range being used on the one hand without accounting for correlated movement information of the heart and CT partial data records of at least one second local frequency range or a complete transformed CT data record being used on the other hand in each instance by selecting a predetermined movement phase of the heart during several heart cycles, back-transforming the new transformed CT data record, and determining and displaying perfusion parameters by using the new CT data records.

In one particular variant of the method according to at least one embodiment of the invention, the CT data records may be projection data records, with a sequence of CT image data records being reconstructed prior to determining the perfusion parameters from the sequence of projection data records.

In an alternative variant of the method according to at least one embodiment of the invention, the CT data records may be image data records, with the newly determined time sequence of image data records being directly used to determine the perfusion parameters.

The method described here can take place in conjunction with different scanning variants, like a spiral scan or a scanning of the patient in the stationary or sequentially displaced circular scan.

In respect of possible transformations of the CT data into a local frequency space, a wavelet transformation can be used for instance, with the local frequency ranges being determined here by the level of the wavelet transformation.

Alternatively, a Fourier transformation can also be used in order to transform the CT data records. The local frequency ranges can in this way be determined by the Fourier coefficients assigned to a local frequency.

Another possibility of transforming the CT data records resides in at least one filtering comprising a local frequency filter from this local frequency range being carried out for each local frequency range.

A computing unit comprising a program memory containing computer program codes, which execute the method according to at least one embodiment of the invention during operation, also belongs to the scope of the invention.

An x-ray CT system comprising a control and computing unit with a program memory containing computer program codes, which executes the method according to at least one embodiment of the invention during operation, likewise also belongs to the invention.

BRIEF DESCRIPTION OF THE DRAWINGS

Embodiments of the invention are described in more detail below with reference to the Figures, with only the features needed to understand the invention being shown. The following reference characters are used here: 1.0: preparation; 1.1: scanning; 1.2: transformation; 1.3: division; 1.4: compilation of a new transformed CT data record; 1.4.1: use of CT partial data records without accounting for correlated movement information; 1.4.1: use of CT partial data records accounting for correlated movement information; 1.5: back-transformation; 1.6: determination of perfusion parameters; C1: X-ray CT system; C2: first x-ray tube; C3: first detector; C4: second x-ray tube (optional); C5: second detector (optional); C6: gantry housing; C7: patient; C8: displaceable patient couch; C9: system axis; C10: control and computing unit; C11: contrast agent applicator; C12: ECG line; C13: control line for the contrast agent applicator; $B_n$: n'th image display; E: ECG curve; FT: transformation; $F_n$: filter for the n'th local frequency range; $g_{n,m}$: weighting factor for the n'th CT partial image or projection data record of the m'th local frequency range; $P_n$: n'th projection data record; $P'_n$: n'th transformed projection data record; $P''_n$: n'th newly compiled transformed projection data record; $P'''_n$: n'th back-transformed projection data record; $Prg_n$: n'th program or program module; R: reconstruction; $RP_n$: resting phase in the heart cycle; $T_{n,m}$: n'th CT partial image or projection data record for the m'th local frequency range; t: time; Z: cycle duration of the heart; $\phi$: angle of rotation of the gantry.

The figures show in detail:

FIG. 5: a schematic representation of the method according to an embodiment of the invention in respect of the data preparation on the basis of reconstructed image data records.

DETAILED DESCRIPTION OF THE EXAMPLE EMBODIMENTS

Figure 1:
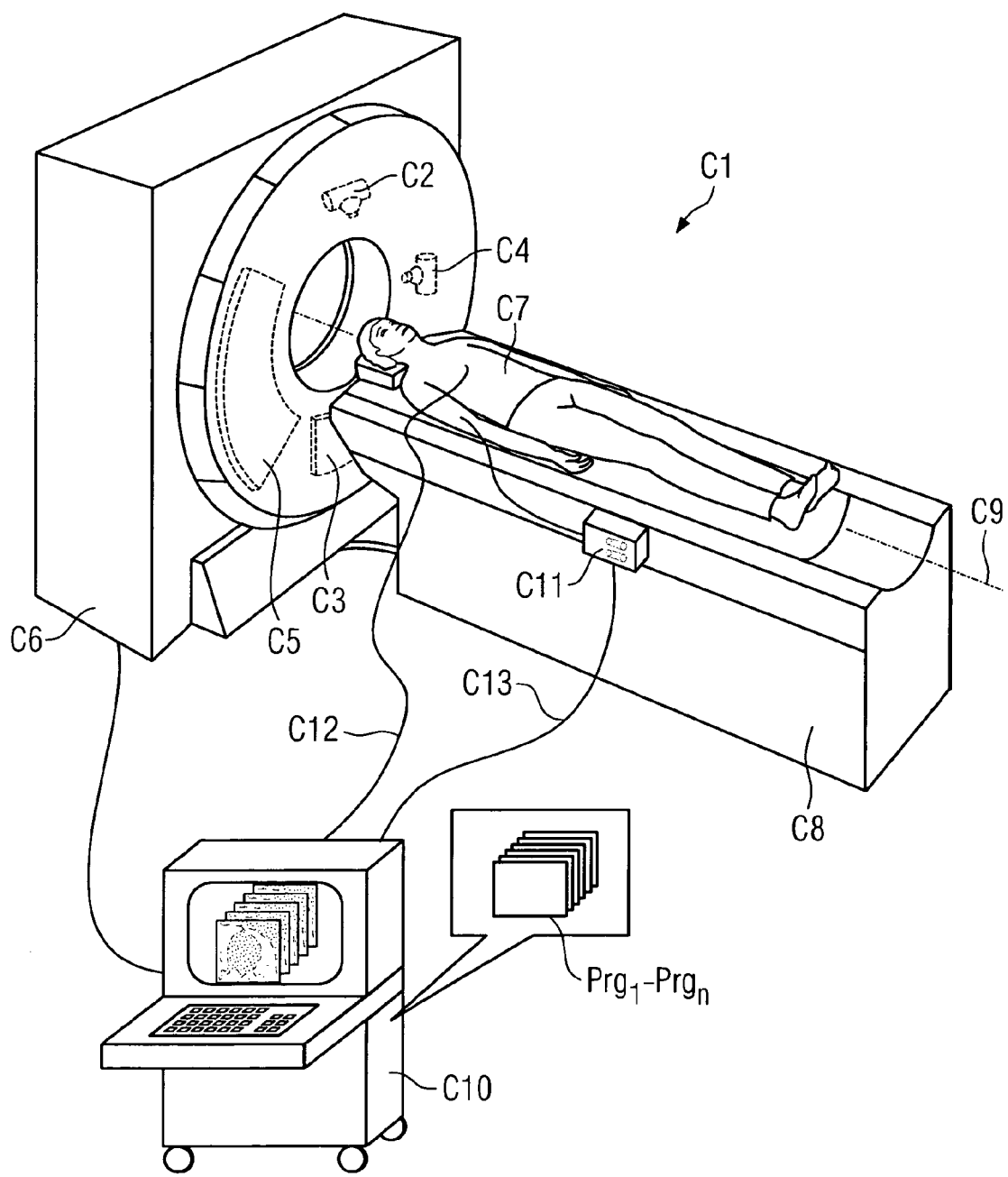
FIG. 1: an x-ray CT system comprising ECG and contrast agent applicator.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an example x-ray CT system C1, which is suited to implementing the method according to an embodiment of the invention. The x-ray CT system C1 consists of a gantry housing C6, in which a gantry (not shown in more detail here) is located, to which a first x-ray tube C2 is fastened with an opposite first detector C3. Optionally a second x-ray tube C4 with an opposite second detector system C5 can also be arranged on the gantry. The use of two or if necessary three tube/detector systems arranged angularly offset if necessary allows for an improved time resolution of the scanning. A patient C7 is positioned on a patient couch C8 which can be displaced in the direction of the system axis C9, with which it can be moved continuously or sequentially during the scanning process along the system axis C9 through a measuring field between the x-ray tubes and the detectors assigned thereto in each instance. If the detector has an adequate width for a provided examination field, there is also the possibility of moving the patient with this examination field, for instance the heart region, into the measuring range of the detector and implementing circular scans there in a stationary fashion, in other words without further displacement. These scanning processes are controlled by means of a computing and control unit C10 with the aid of computer programs $Prg_1$ to $Prg_n$. Additionally, the heart potentials of the patient C7 can be recorded during the scanning process with the aid of an ECG line C12 so that the temporally correlated information can be stored between the recorded CT data records and the heart movement. The reconstruction can likewise take place in the computing and control unit C10.

Furthermore, contrast agent can be applied to the patient prior to or during the scanning process with the aid of a contrast agent applicator C11, which is connected to the control and computing unit C10 by way of a control line C13. The perfusion of the contrast agent can be examined in a manner known per se by examining this contrast agent in the heart region and medically relevant perfusion parameters can be determined in a manner known per se.

In accordance with an embodiment of the invention, computer programs, in which the previously described method can be implemented with the aid of the CT system shown here, are found in the memory.

Figure 2:
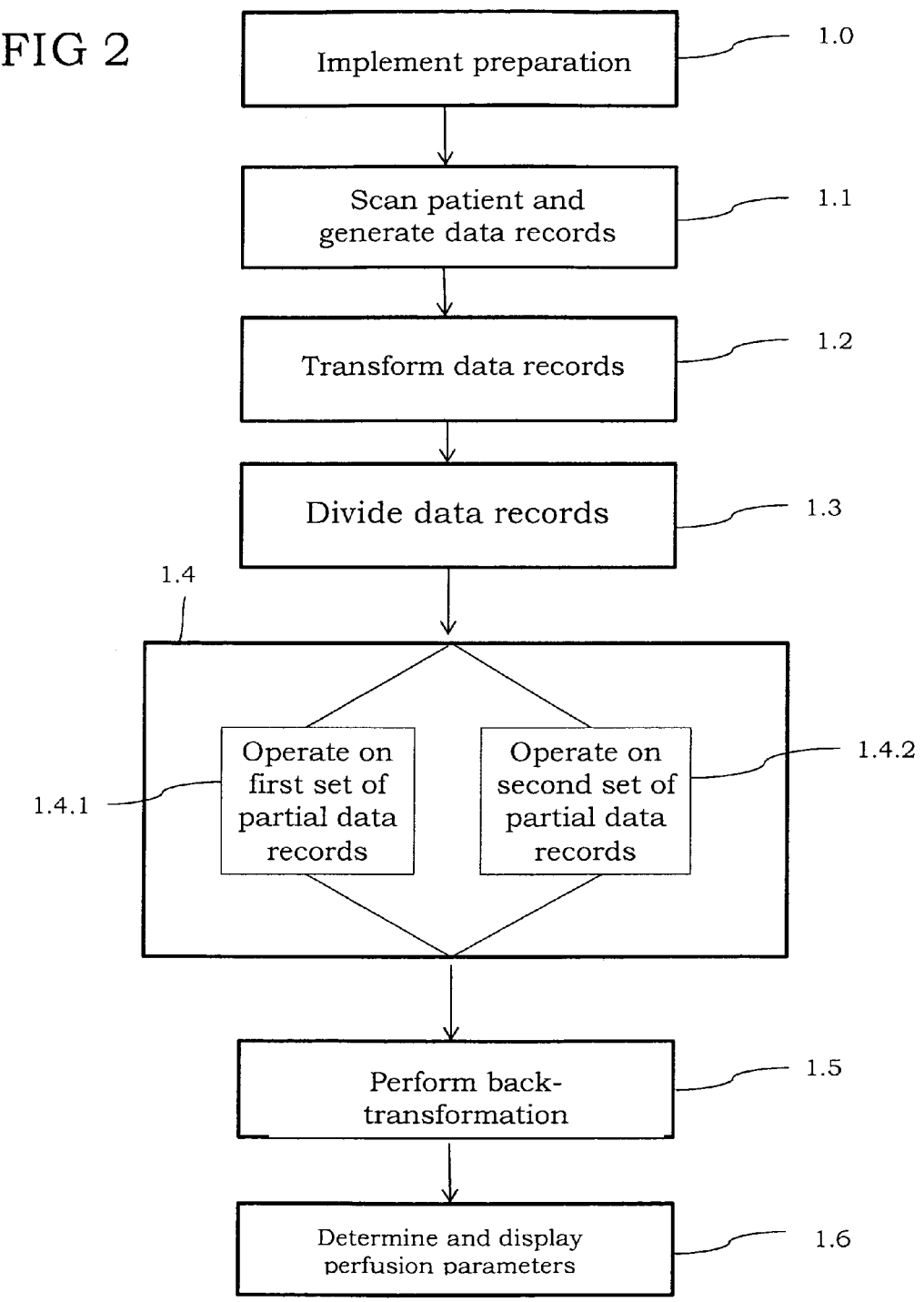
FIG. 2: a flowchart of a preferred process flow.

The method according to an embodiment of the invention is shown in a preferred embodiment in FIG. 2 in the form of a flowchart. In method step 1.0, the preparation is implemented here in order to implement the actual method, with it being possible to apply contrast agent for instance. With method step 1.1, the patient is scanned with an x-ray CT system in the region of the beating heart and CT data records with correlated movement information of the heart are generated during several heart cycles, which in turn contain several cycle phases. A transformation of the CT data records to a local frequency space is then carried out in method step 1.2. By way of example, this transformation may be a Fourier transformation or a wavelet transformation.

Because the CT data records now exist in a transformed state, a division of the CT data records into several transformed CT data records is performed in method step 1.3 in accordance with different local frequency ranges. It is therefore now possible to treat the information available in the individual CT partial data records differently. This takes place in method step 1.4 in which a compilation of a new transformed CT data record from several partial data records takes place again, with all partial data records no longer being used unseen but being used instead according to the subordinate method steps 1.4.1 and 1.4.2 of CT partial data records of a certain local frequency range on the one hand without accounting for correlated movement information of the heart and of CT partial data records of another local frequency range or also a completely transformed CT data record on the other hand, both however being used during several heart cycles if a predetermined movement phase of the heart is missing in each instance. Attention is also paid by selecting certain CT partial data records from certain local frequency ranges for the data from existing data records to be used for image production, which positively contribute toward the image production, while other data, which contributes to a movement blur, is removed. Additionally, attention can also be paid during the compilation of the partial data records for instance to ensure that CT partial data records from local frequency ranges are weighted particularly significantly, the latter containing information in the region of the local frequencies of typical perfusion changes. This information is as a result emphasized particularly clearly so that it is also easily identifiable in the resultant images.

According to the following method step 1.5 a back-transformation of the previously compiled new transformed CT data record is now carried out so that a time sequence of CT data records can then be formed with the aid of additional CT data records which have developed in this way.

In method step 1.6, the determination and display of perfusion parameters now takes place by using CT data records, which were formed in accordance with the afore-described embodiment of the method.

The previously described method embodiment can basically be applied both to raw data, in other words to projection data; there is however also the possibility of applying this method to already previously reconstructed image data, so that reconstruction of the projection data records into image data records is then no longer necessary.

Figure 3:
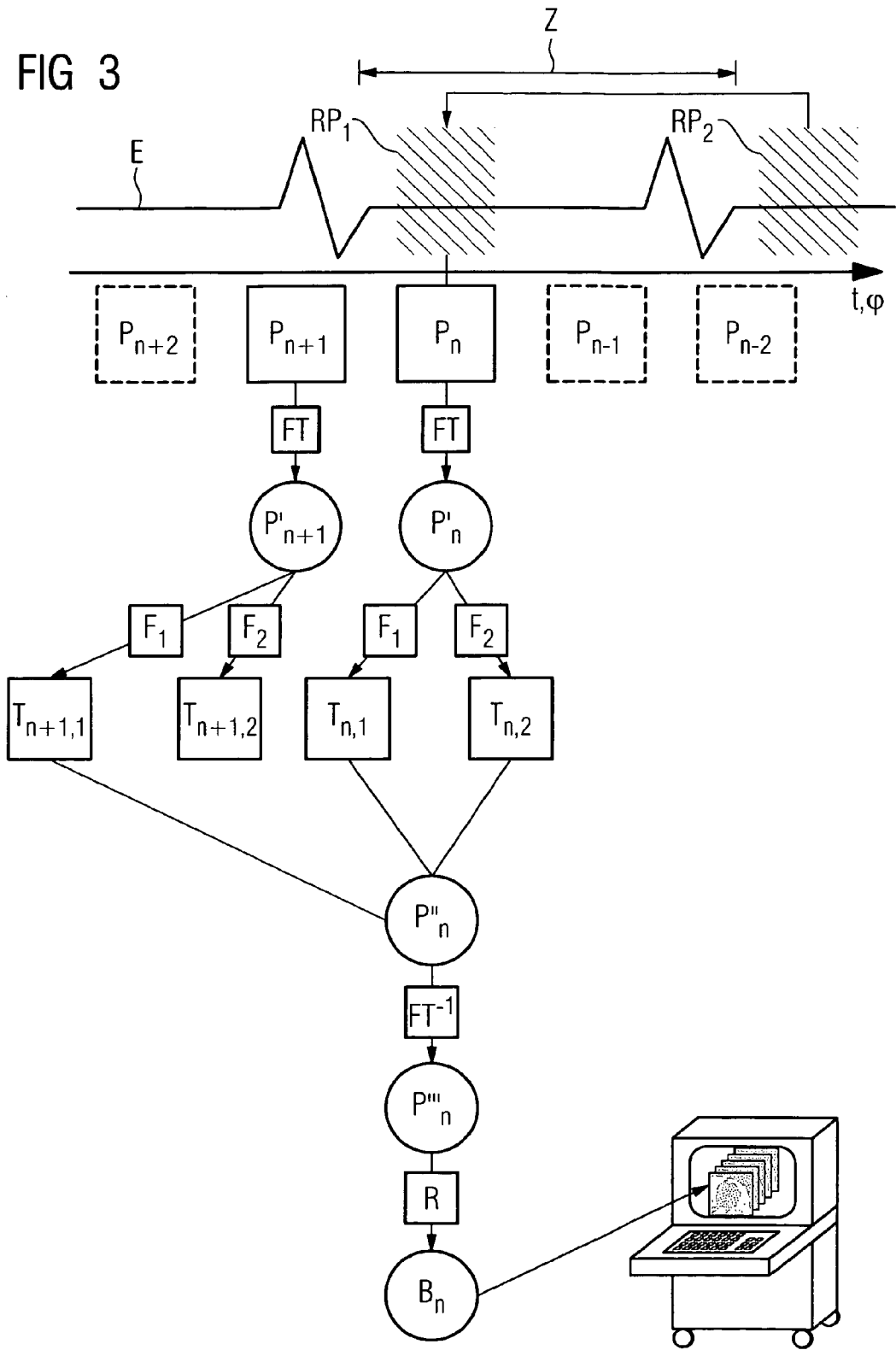
FIG. 3: a schematic representation of a simple variant of the method according to an embodiment of the invention in respect of the data preparation on the basis of projection data records.

One simple variant of the previously described method embodiment is shown in FIG. 3, which indicates a schematic representation in particular in respect of the data preparation on the basis of projection data records. A curve of an ECG E is shown above the time bar, which represents the advance of the scanning time t and/or of the rotary angle φ of the gantry. Resting phases $RP_1$ and $RP_2$ and the duration of a heart cycle Z are shown as hatched within this ECG. Projection data records $P_{n+2}$ to $P_{n-2}$ are collected during the data acquisition. In the example shown, the projection data $P_n$ is also extended by additional measurements from the resting phases $RP_2$ of other cycles of the heart, so that a complete projection data record is produced overall.

In accordance with an embodiment of the invention, the two projection data records $P_n$ and $P_{n+1}$ are now subjected to a transformation, in the present example a Fourier transformation FT, and are projected into the local frequency space so that the transformed projection data records and P', are produced. A division of the transformed projection data records into partial projection data records $T_{n+1,1}$, $T_{n+1,2}$, $T_{n,1}$ and $T_{n,2}$ then ensues. The indexes mentioned second here represent a certain frequency range $F_1$ and/or $F_2$, in each instance which is shown in the relevant partial projection data records.

In accordance with an embodiment of the invention, a new transformed projection data record $P''_n$ is now compiled from the afore-cited partial projection data records, with, in the present example, account no longer being taken of the partial projection data record $T_{n+1,2}$ in the case of the new compilation, since this data corresponds to a local frequency which corresponds to the movement frequency of the heart, which is to be suppressed as much as possible in the new projection data record since too much blurring occurs otherwise. The new transformed projection data record $P''_n$ is then subjected to a back-transformation $FT^{-1}$, so that a new back-transformed projection data record $P'''_n$ develops which is then subjected to a reconstruction R so that an image $B_n$ can be displayed.

This method can now be implemented by way of a plurality of advancing time instants, so that a series of images is generated, on the basis of which a perfusion measurement can be implemented.

Figure 4:
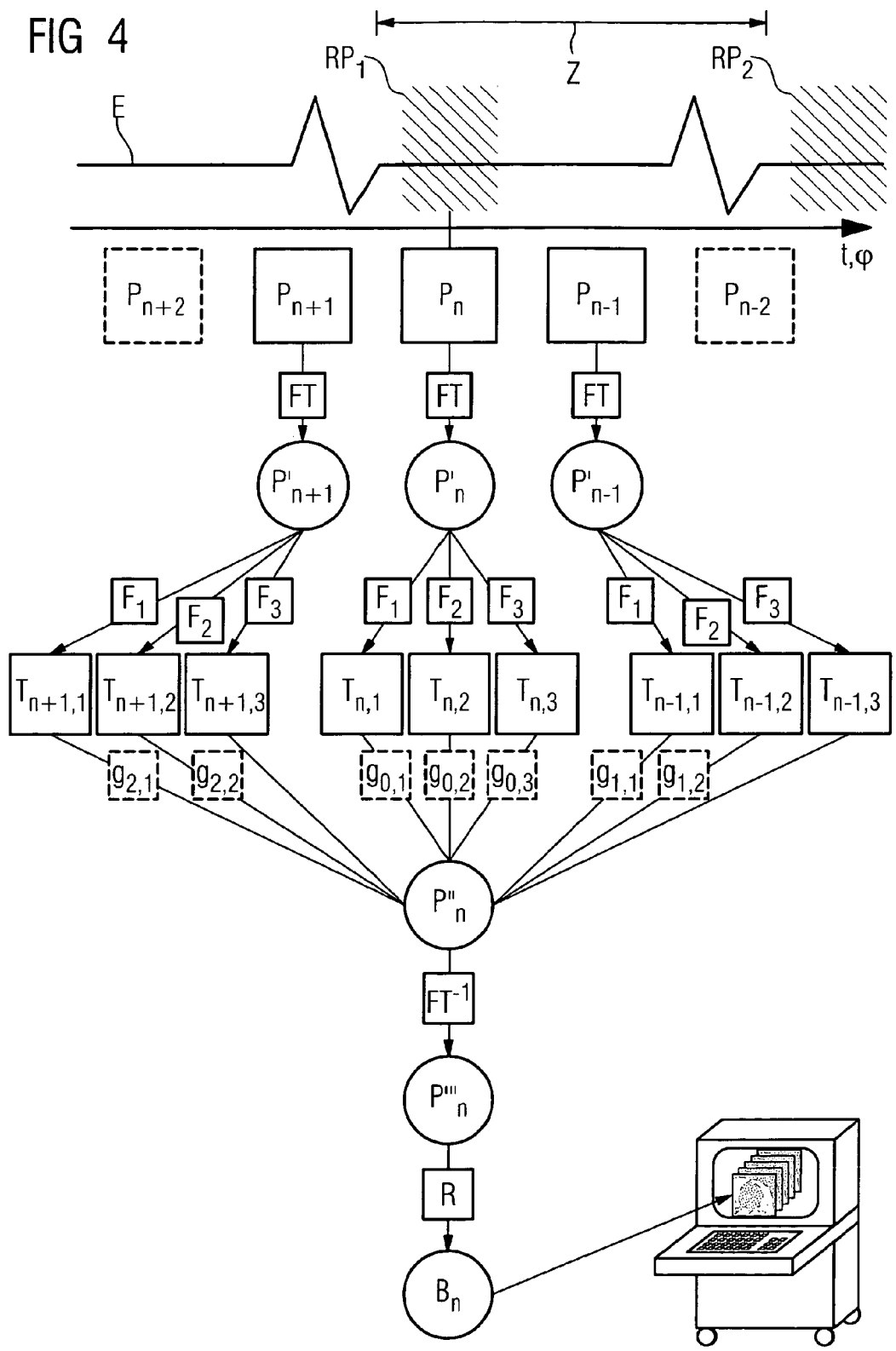
FIG. 4: a schematic representation of the method according to an embodiment of the invention with a weighted compilation of partial CT data records in respect of the data preparation on the basis of projection data records with subsequent reconstruction.

FIG. 4 shows a slightly more complex variant of the application of an embodiment of the inventive method to projection data records. Contrary to FIG. 3, no cross-cycle collection of projection data from the resting phases is carried out here in the projection data record $P_n$. Projection data is however collected overall over a larger range of the heart cycle, the data being represented here by the three projection data $P_{n+1}$, $P_n$ and $P_{n-1}$. A Fourier transformation of the individual projection data records then takes place again, it being noted that an embodiment of the inventive method is not exclusively restricted to Fourier transformations.

The transformed projection data records $P'_{n+1}$ to $P'_{n-1}$ are then divided again into transformed partial projection data records, which can then be compiled to form a new transformed projection data record $P''_n$ weighted with the weighting factors $g_{n,m}$. Here too, the partial projection data records $T_{n+1,3}$ und $T_{n-1,3}$ are as a result completely suppressed since these are unwanted local frequencies, whereas the remaining partial projection data records are used completely. The partial projection data record $T_{n,3}$ is used exclusively to form the new projection data record, since this image information originates from the resting phase $RP_1$ of the heart cycle Z and hardly any movement blurs can thus occur.

The selection of the weighting factors $g_{n,m}$ can also be configured here such that in particular local frequencies which lie in the region of the typical local frequencies of perfusion changes, are increasingly adopted so that this information occurs more clearly in the newly formed projection data record $P''_n$. A back-transformation $FT^{-1}$ to a new back-transformed projection data record $P'''_n$ including a reconstruction R and display of an image $B_n$, then takes place again. According to the representation in FIG. 3, an embodiment of this method can also be applied repeatedly to different time instants, so that a series of images is produced, on the basis of which the determination of perfusion parameters can be performed particularly favorably.

Similarly to FIG. 4, the method according to an embodiment of the invention is shown in FIG. 5, with the transformation and local frequency distribution nevertheless not occurring here at projection data level but instead at an image data level. Image data $B_{n+1}$ to $B_{n-1}$ is accordingly calculated from the projection data records $P_{n+1}$ to $P_{n-1}$ firstly with the aid of a generally known reconstruction algorithm. A transformation FT into the local frequency space then takes place, so that the transformed image data $B'_{n+1}$ to $B'_{n-1}$ is produced there. A breakdown into transformed partial image data records $T_{n,m}$ then takes place with a subsequent new compilation of a new transformed image data record $B''_n$ resulting therefrom, it being possible for individual weighting factors to be used here for instance during the evaluation of all partial image data records, with frequency ranges, which result in local blurs being drastically reduced and local frequency ranges, which result in an improved information representation of the perfusion, on the other hand being evaluated in more detail.

A new CT image data record $B''_n$ results overall, which is back-transformed from the local frequency space by way of an inverse transformation function $FT^{-1}$ into the local space so that a new image data record $B'''_n$ results which can be shown on a computing system for instance. If this afore-cited method is used for different time instants, a series of images is produced, on the basis of which the desired perfusion parameters are displayed more clearly, since the noise-to-signal ratio was reduced as far as possible and on the other hand movement blurs were removed from the existing image data.

It is apparent that the previously cited features of embodiments of the invention can be used not only in the respectively cited combination but instead also in other combinations or alone, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating computed tomography image data records of a patient in a heart CT scan for a perfusion control by applying contrast agent comprising:
scanning the patient in a region of a beating heart using an X-ray CT system and generating CT data records with correlated movement information of the heart during several heart cycles with several cycle phases;
transforming the generated CT data records into a local frequency space;
dividing at least one transformed CT data record into at least two transformed CT partial data records, in each instance according to different local frequency ranges;
compiling a new transformed CT data record from several CT partial data records in each instance, with CT partial data records of at least one first local frequency range being used without accounting for correlated movement information of the heart and CT partial data records of at least one second local frequency range or a complete transformed CT data record being used by selecting a predetermined movement phase of the heart during several heart cycles in each instance;
back-transforming the new transformed CT data record; and
determining and indicating perfusion parameters by using the back-transformed new CT data records.

2. The method as claimed in claim 1, wherein the CT data records are projection data records and a time sequence of CT image data records is reconstructed from the time sequence of projection data records prior to determining the perfusion parameters.

3. The method as claimed in claim 2, wherein the scanning takes place in spiral operation.

4. The method as claimed in claim 2, wherein the scanning takes place in the stationary circular scan.

5. The method as claimed in claim 2, wherein the scanning takes place in the sequential circular scan.

6. The method as claimed in claim 2, wherein at least one filtering with a local frequency filter from the local frequency range is implemented for each local frequency range in order to transform the CT data records.

7. The method as claimed in claim 1, wherein the CT data records are image data records, which are used directly as a time sequence of image data records to determine the perfusion parameters.

8. The method as claimed in claim 7, wherein the scanning takes place in spiral operation.

9. The method as claimed in claim 7, wherein the scanning takes place in the stationary circular scan.

10. The method as claimed in claim 7, wherein the scanning takes place in the sequential circular scan.

11. The method as claimed in claim 7, wherein at least one filtering with a local frequency filter from the local frequency range is implemented for each local frequency range in order to transform the CT data records.

12. The method as claimed in claim 1, wherein the scanning takes place in spiral operation.

13. The method as claimed in claim 1, wherein the scanning takes place in the stationary circular scan.

14. The method as claimed in claim 1, wherein the scanning takes place in the sequential circular scan.

15. The method as claimed in claim 1, wherein a wavelet transformation is used to transform the CT data records.

16. The method as claimed in claim 15, wherein the local frequency ranges are determined by the level of the wavelet transformation.

17. The method as claimed in claim 1, wherein a Fourier transformation is used to transform the CT data records.

18. The method as claimed in claim 17, wherein the local frequency ranges are determined by the Fourier coefficients assigned to a local frequency.

19. The method as claimed in claim 1, wherein at least one filtering with a local frequency filter from the local frequency range is implemented for each local frequency range in order to transform the CT data records.

20. A computing unit, comprising:
a program memory, computer program code being stored in the program memory, the computer program code being adapted to implement the method of claim 1 during operation of the computing unit.

21. The x-ray CT system, comprising:
a control and computing unit including a program memory, computer program code being stored in the program memory, the computer program code being adapted to implement the method of claim 1 during operation of the x-ray CT system.

22. A computer readable medium including program segments for, when executed on a computer device, causing the computer device to implement the method of claim 1.

* * * * *